United States Patent [19]

Wideman

[11] Patent Number: 4,678,544
[45] Date of Patent: Jul. 7, 1987

[54] PROCESS FOR THE SEPARATION OF 2MBA FROM MIPK

[75] Inventor: Lawson G. Wideman, Tallmadge, Ohio

[73] Assignee: The Goodyear Tire & Rubber Company, Akron, Ohio

[21] Appl. No.: 834,687

[22] Filed: Feb. 28, 1986

[51] Int. Cl.⁴ .......................... B01D 3/34; B01D 3/36
[52] U.S. Cl. ........................... 203/95; 568/410; 203/96
[58] Field of Search ............... 568/410; 585/606, 324; 203/96, 95

[56] References Cited

U.S. PATENT DOCUMENTS

| | | | |
|---|---|---|---|
| 2,607,719 | 8/1952 | Eliot | 203/96 |
| 3,303,108 | 2/1967 | Rauch | 203/96 |
| 3,625,836 | 12/1971 | Stansbury | 568/410 X |
| 3,647,903 | 3/1972 | Maurin | 585/606 X |
| 4,163,696 | 8/1979 | Wong | 568/410 X |
| 4,524,233 | 6/1985 | Hsu | 585/606 |

OTHER PUBLICATIONS

Classification Definitions; U.S. Patent Office, 12/1965, pp. 203–226; copy in group 130.

Primary Examiner—Kenneth M. Schor
Attorney, Agent, or Firm—D. O. Nickey

[57] ABSTRACT

This invention is directed to the discovery that the distillative separation of 2-methylbutanal (2MBA) from a mixture containing methylisopropylketone (MIPK) and 2MBA can be greatly enhanced by the addition of water to the mixture.

4 Claims, No Drawings

PROCESS FOR THE SEPARATION OF 2MBA FROM MIPK

TECHNICAL FIELD

This invention relates to the discovery that the presence of water in a 2MBA/MIPK mixture will greatly assist in the economical and efficient distillation of 2MBA from the mixture.

BACKGROUND ART

Numerous methods have been developed over the years to produce isoprene. One method described in U.S. Pat. No. 4,524,233, herein incorporated by reference, discloses the dehydration reaction of 2-methylbutanal (2MBA) over an acid dehydration catalyst such as boron phosphate to yield isoprene. As disclosed in U.S. Pat. No. 4,524,233, a major by-product of the 2MBA dehydration is methylisopropylketone,(MIPK). For the economical operation of a process as described in this U.S. patent, it will be required to recycle the 2MBA that is not converted to MIPK or isoprene back to the dehydration reactor.

The close boiling points of 2MBA (90°-92° C.) and MIPK (92°-94° C.) will make separation by distillation difficult. Such a separation of two compounds having such a close boiling point would be known to those skilled in this art to present extreme difficulties for the efficient and economic separation of the 2MBA from the mixture.

The inventor herein has unexpectedly found that a mixture of 2MBA and MIPK can be separated to give high purity 2MBA by selectively azeotroping 2MBA with water. The resulting high purity 2MBA is easily phase separated from the azeotroping water and recycled to the dehydration reactor. None of the prior art suggests or discloses this unique discovery.

DISCLOSURE OF THE INVENTION

There is disclosed a process for the distillative separation of 2MBA from a mixture comprising 2MBA and methylisopropyl ketone, the improvement comprising adding water to said mixture in an amount from 5 to 50 percent by weight of the mixture prior to the distillation.

There is also disclosed a process for distillative separation of 2-methylbutanal from a mixture comprising 5 to 85 parts by weight of methylisopropylketone and from 5-95 parts by weight of 2-methylbutanal, said process comprising the distillative separation of the 2-methylbutanal from the mixture in the presence of water; said water being present in an amount from 5 to 50% by weight of the mixture.

The composition of the effluent from the aldehyde to diene dehydration reactor contains isoprene, MIPK, 2MBA, and water in addition to other minor byproducts. A typical single pass effluent analysis from the dehydration reaction contains about 2 to 3% by weight MIPK, however, as the 2MBA/MIPK is recycled the level of MIPK increases to a point where the yield of isoprene is greatly diminished per pass over the catalyst. In order to increase the yield of isoprene per pass the level of MIPK in the recycle must be reduced.

In a simple fractionation, the isoprene is easily removed from the reactor effluent leaving a mixture of 2MBA and MIPK to be recycled to the dehydration reactor. It is advantageous in the aldehyde to diene dehydration that the aldehyde be as pure as possible thus insuring the highest level of isoprene production, since the presence of MIPK in the aldehyde feed has been shown to be detrimental to the efficient production of isoprene. The following examples are intended to illustrate and not to limit the scope of the invention.

BEST MODE OF THE INVENTION

A 33 cm × 1.9 cm distillation column containing stainless steel rope packing was utilized in the following examples 1-4.

EXAMPLE 1

A mixture consisting of 190 g of 2MBA, 20 g of MIPK and 100 g of water was charged to the distillation pot. The pot at the bottom of the distillation column was heated to the reflux point of the mixture and distillation cuts were taken after equilibrium was achieved within the distillation column. The initial concentration of the organic components in the distillation pot was analyzed by gas chromatography and was determined to consist of 91.2% 2MBA and 8.7% MIPK by weight. The distillation cut taken overhead was phase separated and the organic phase consisted of 98.3% 2MBA and 1.4% MIPK by weight.

EXAMPLE 2

100 g of 2MBA, 100 g of MIPK and 100 g of water were charged to the distillation pot. After reflux was obtained, the overhead organic fraction analyzed to be 91.6% 2MBA and 8.4% MIPK by weight.

EXAMPLE 3

A mixture of 20 g of 2MBA, 190 g of MIPK and 100 g of water were charged to the distillation pot. After attainment of reflux the overhead organic fraction analysis indicated 62.6% 2MBA and 37.4% MIPK by weight.

EXAMPLE 4—CONTROL

To the distillation pot was charged 100 g of 2MBA and 100 g of MIPK. The analysis of the overhead fraction indicated a composition consisting of 59.7% 2MBA and 39.6% MIPK by weight.

These examples 1, 2 and 3 compared to the control, (Example 4) quite evidently demonstrate the beneficial effects that can be obtained through the addition of water to the mixture to be distilled.

In all examples 1-3, the amount of water that is phase separated from the overhead fraction is about 10% of the overhead fraction by volume. It was the organic portion after phase separation that was analyzed by gas chromatography for chemical composition. Further, the presence of water lowered the distillation head temperature to 77° C. in examples 1-3, while without the use of water, the distillation head temperature is about 91°-94° C. (Example 4—Control).

It is quite evident that the close boiling points of MIPK and 2MBA make separation by conventional distillation impractical, and thus, the instant invention would have utility in the separation of 2MBA from MIPK.

EXAMPLE 5—CONTROL

To a 2.74 meter distillation column having a 48 theoretical plate rating was charged 800 ml of a mixture consisting of 85% MIPK by weight and 15% 2MBA by weight.

The distillation column was heated and reflux was obtained, and at 6, 8 and 10 hours, analysis of the overhead product and the composition of the distillation pot were conducted by gas chromatography. After 6 hours of reflux, the overhead composition taken at 91° C. consisted of 60.72% 2MBA and 39.28% MIPK. The composition of the pot was 13.56% 2MBA and 86.44% MIPK. The temperature of the pot was 94° C. In a similar manner, after 8 hours of reflux, the overhead composition consisted of 61.43% 2MBA and 38.57% MIPK while the pot composition was 13.89% 2MBA and 86.11% MIPK. After 10 hours of reflux the overhead composition consisted of 61.6% 2MBA and 38.4% MIPK. The pot composition was 13.26% 2MBA and 86.74% MIPK. After 23 hours of reflux 100.3 weight percent accountability for the 2MBA and MIPK were obtained. This indicates that no reaction between MIPK and 2MBA was taking place in the pot.

EXAMPLE 6

In the 2.74 meter distillation column having 48 theoretical plates was charged 800 ml of a mixture consisting of 85% MIPK by weight and 15% 2MBA by weight. In addition thereto there was charged 200 ml of water. After the attainment of reflux, samples were taken from the overhead product and the distillation pot at 6, 8 and 10 hours. After 6 hours, the organic overhead composition consisted of 97.32% 2MBA and 2.68% MIPK. The overhead temperature was 77° C. The pot organic composition after 6 hours was 10.3% 2MBA and 89.7% MIPK. After 8 hours of reflux, the overhead organic composition was 98.7% 2MBA and 1.3% MIPK. The pot organic composition was 9.68% 2MBA and 90.32% MIPK. After 10 hours of reflux, the overhead organic composition was 98.82% 2MBA and 1.18% MIPK at a head temperature of 77° C. The pot organic composition was 10.06% 2MBA and 89.94% MIPK at a temperature of 80° C.

It is quite evident from these examples and the controls that the instant invention will enormously benefit the separation of 2MBA from its mixture with MIPK. The lowering of the distillation temperatures and the substantial increase in purity will provide definite economic advantages to any process which converts or dehydrates 2MBA to isoprene.

Although the present invention has been described herein with reference to the preferred typical embodiments thereof, it will be apparent to those skilled in the art that there may be modifications made in the process.

We claim:

1. A process for the distillative separation of 2-methylbutanal from a mixture consisting of from 5 to 85 parts by weight of methylisopropylketone and from 15 to 95 parts by weight of 2-methylbutanal, said process consisting of adding water to said mixture in an amount from 5 to 50% by weight based on the weight of the mixture prior to the distillative separation, then the mixture is distilled in a distillation column which is operated under conditions of temperature and pressure such that a 2-methylbutanal/water azeotrope is taken overhead and thereafter the resultant 2-methlybutanal/water distillate is phase separated to isolate essentially pure 2-methylbutanal.

2. The process of claim 1 wherein the water is present in an amount from 10–40% by weight.

3. The process of claim 1 wherein the water is present in an amount from 20–30% by weight.

4. The process of claim 1 wherein the mixture consists of 10–30 parts by weight of methylisopropylketone.

* * * * *